US009578935B2

(12) United States Patent
Horgan

(10) Patent No.: US 9,578,935 B2
(45) Date of Patent: Feb. 28, 2017

(54) ANTISEPTIC BRACELET

(71) Applicant: Jason Horgan, Davie, FL (US)

(72) Inventor: Jason Horgan, Davie, FL (US)

(*) Notice: Subject to any disclaimer, the term of this patent is extended or adjusted under 35 U.S.C. 154(b) by 0 days.

(21) Appl. No.: 14/882,311

(22) Filed: Oct. 13, 2015

(65) Prior Publication Data
US 2016/0044997 A1 Feb. 18, 2016

Related U.S. Application Data

(63) Continuation-in-part of application No. PCT/US2014/033703, filed on Apr. 10, 2014.

(60) Provisional application No. 61/810,308, filed on Apr. 10, 2013.

(51) Int. Cl.
B67D 7/84 (2010.01)
A44C 5/00 (2006.01)
A45D 34/00 (2006.01)
A61M 35/00 (2006.01)
A47K 5/12 (2006.01)
A45C 11/00 (2006.01)
A45F 5/00 (2006.01)

(52) U.S. Cl.
CPC ............... *A44C 5/003* (2013.01); *A45D 34/00* (2013.01); *A47K 5/1201* (2013.01); *A61M 35/003* (2013.01); *A44C 5/0023* (2013.01); *A45C 2011/007* (2013.01); *A45F 2005/008* (2013.01)

(58) Field of Classification Search
CPC ....... A44C 5/003; A44C 5/0023; A45D 34/00; A47K 5/1201; A61M 35/003; A45C 2011/007; A45F 2005/008

USPC ......................................................... 222/175
See application file for complete search history.

(56) References Cited

U.S. PATENT DOCUMENTS

| 5,924,601 | A | * | 7/1999 | Chen | F41H 9/10 222/175 |
| 7,735,682 | B1 | * | 6/2010 | Cassel | A47K 10/38 221/155 |
| 8,328,055 | B1 | * | 12/2012 | Snyder | A45F 5/00 224/197 |
| 2004/0111071 | A1 | * | 6/2004 | Powers | A45D 34/00 604/310 |
| 2006/0091156 | A1 | * | 5/2006 | Powers | A45D 34/00 222/175 |
| 2006/0219742 | A1 | * | 10/2006 | Chen | A44C 5/003 224/148.4 |
| 2008/0230560 | A1 | * | 9/2008 | Powers | A45D 34/00 222/175 |
| 2009/0134184 | A1 | * | 5/2009 | Stollmann | A44C 5/003 222/78 |

(Continued)

Primary Examiner — J. Casimer Jacyna
Assistant Examiner — Benjamin R Shaw
(74) Attorney, Agent, or Firm — The Keys Law Firm PLLC

(57) ABSTRACT

A wearable bracelet containing an antiseptic solution that can be selectively dispensed by a user as desired to assist in disinfecting the user's hands or other surface. The antiseptic bracelet is to be worn on and around user's wrist near the base of the user's palm and comprises a bracelet band that is connected to opposing sides of a dispensing pod, forming a loop which can be placed around a user's wrist. The dispensing pod includes a hollow interior forming an internal reservoir and a dispensing tip positioned in an outlet channel. The internal reservoir enables the dispensing pod to hold an antiseptic solution and dispensing tip enables a user to selectively dispense a portion of the solution in the dispensing pod.

9 Claims, 11 Drawing Sheets

(56) References Cited

U.S. PATENT DOCUMENTS

| | | | | |
|---|---|---|---|---|
| 2009/0265971 | A1* | 10/2009 | Cook | G09F 3/005 |
| | | | | 40/633 |
| 2011/0155765 | A1* | 6/2011 | Properzi | A47K 5/1201 |
| | | | | 222/175 |
| 2012/0138637 | A1* | 6/2012 | Ciavarella | A44C 5/0023 |
| | | | | 222/175 |
| 2012/0282011 | A1* | 11/2012 | Francois | A61L 2/18 |
| | | | | 401/196 |
| 2015/0233681 | A1* | 8/2015 | Olah | F41H 9/10 |
| | | | | 222/1 |

* cited by examiner

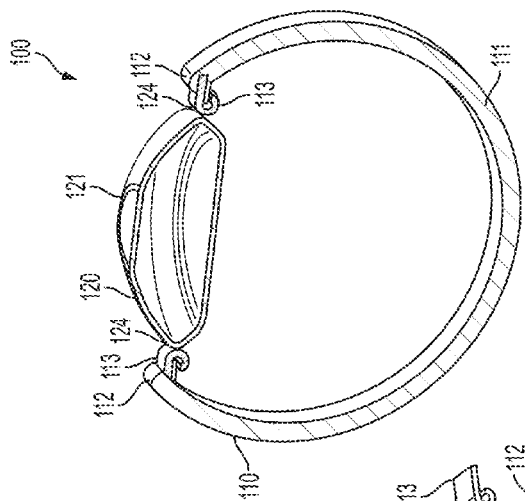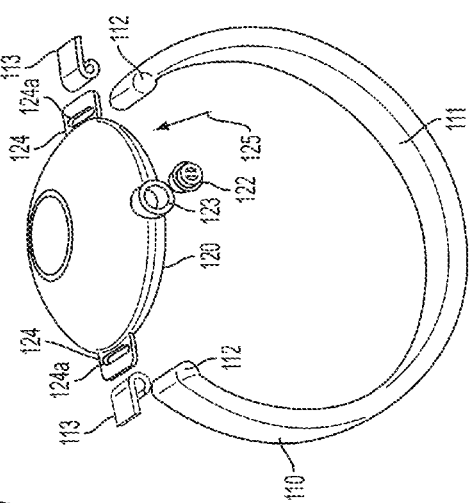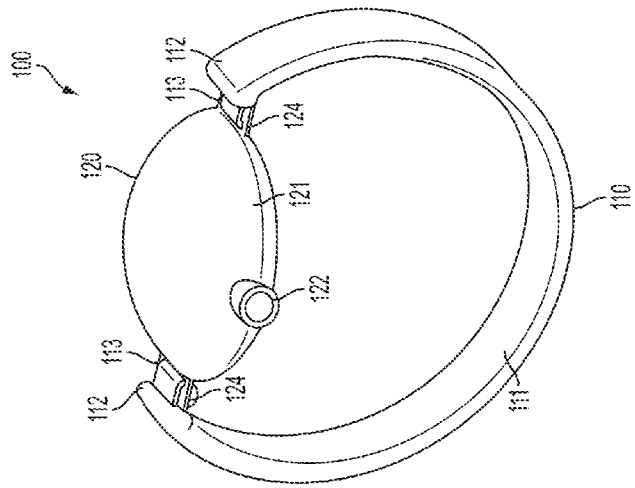

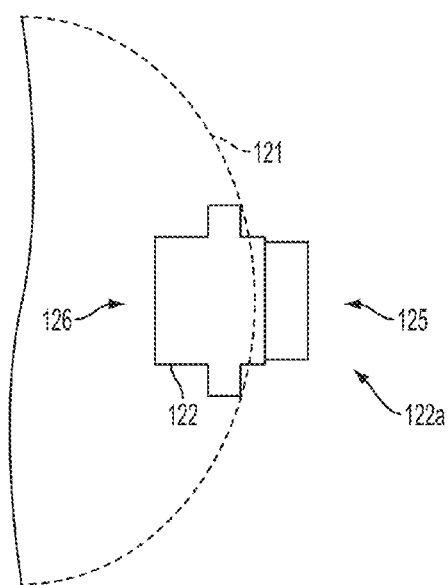 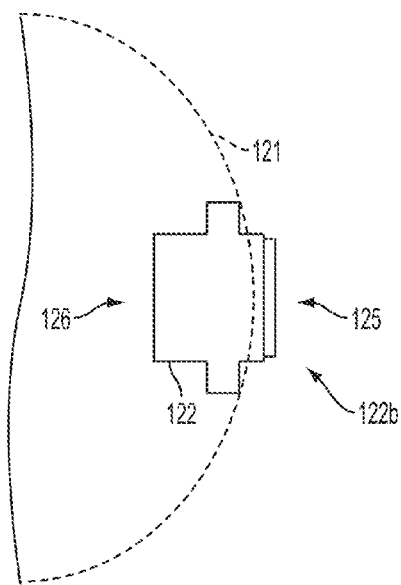
FIG. 12A  FIG. 12B
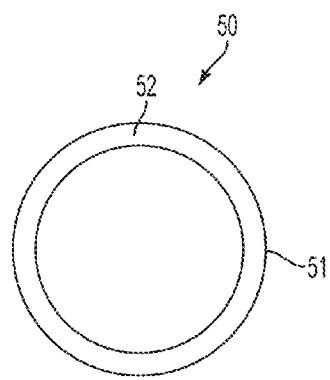 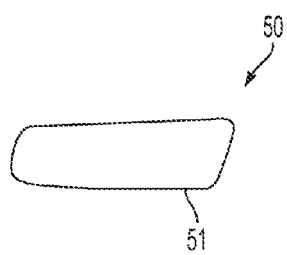
FIG. 13A  FIG. 13B

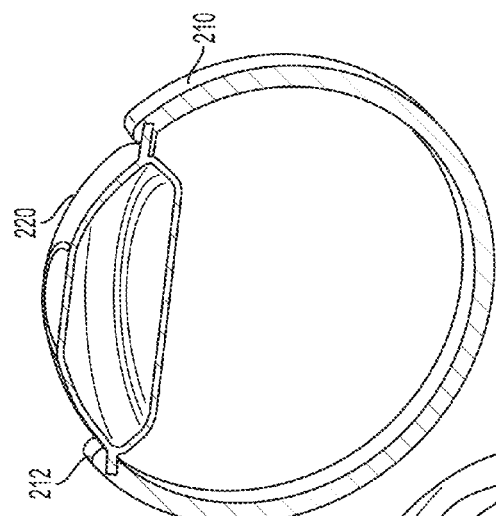
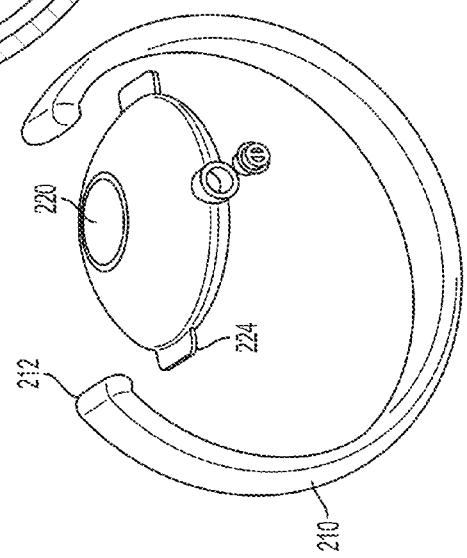
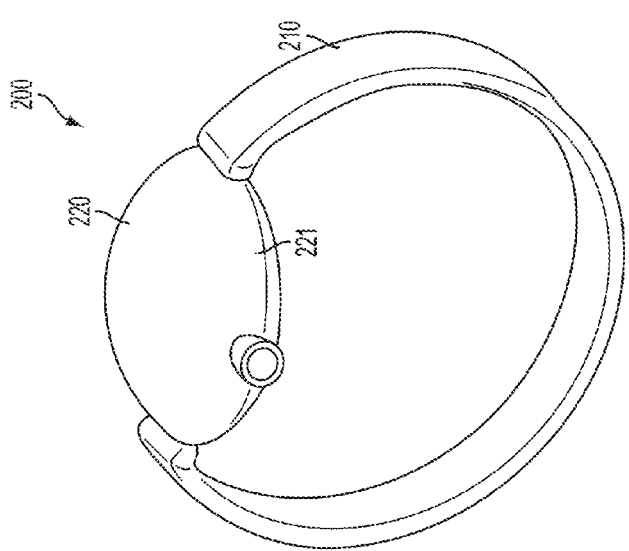

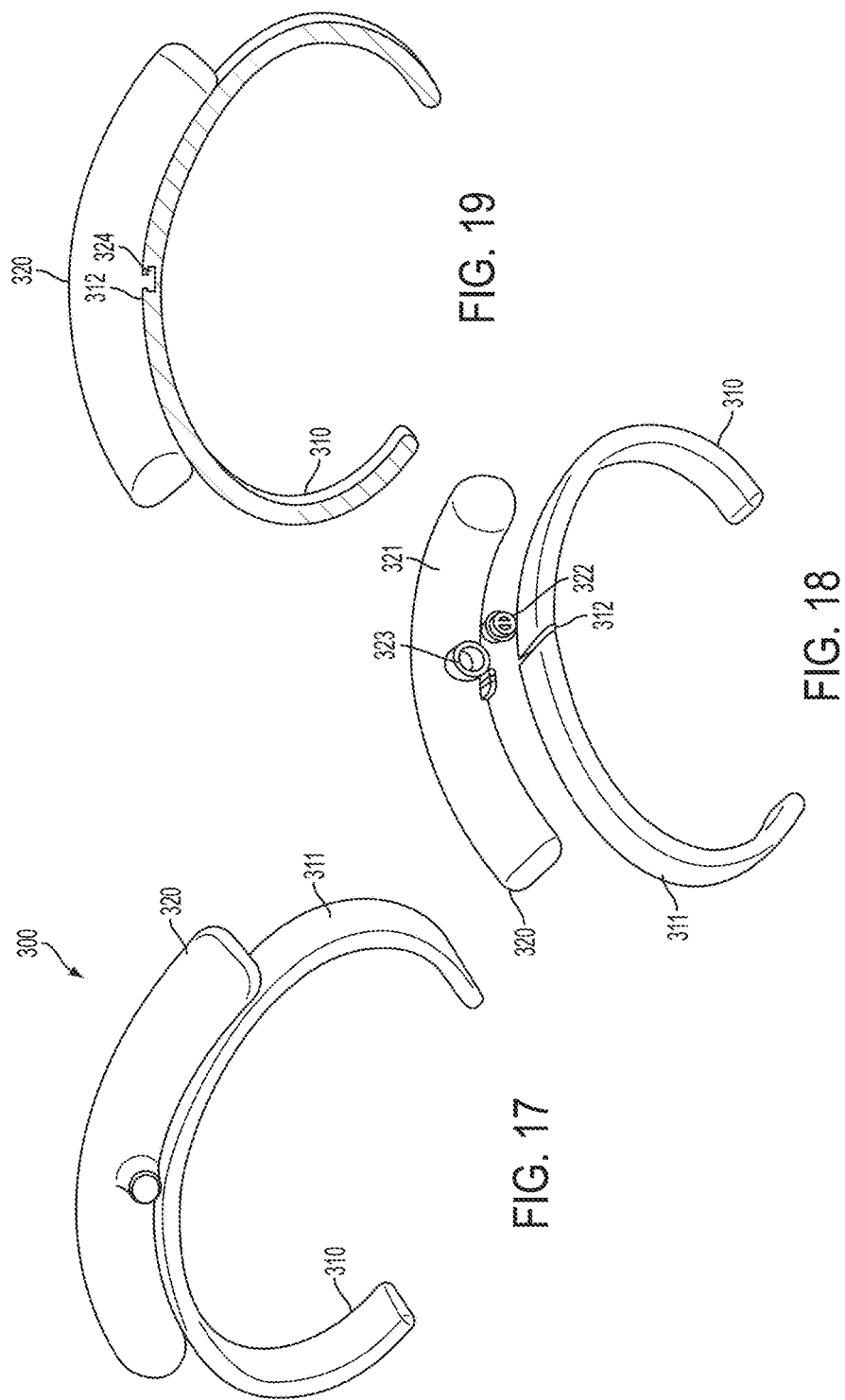

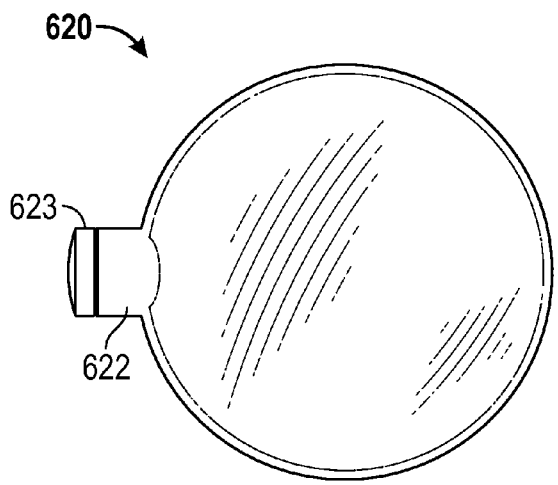
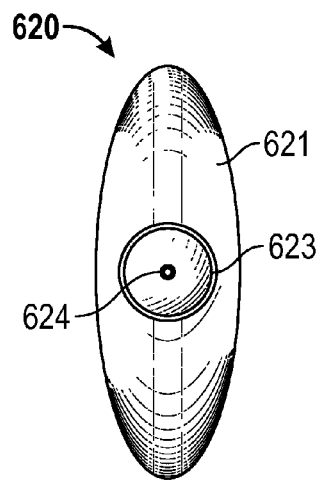
FIG. 28  FIG. 29
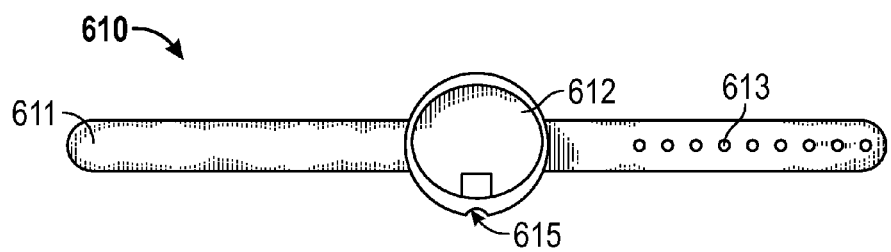
FIG. 30
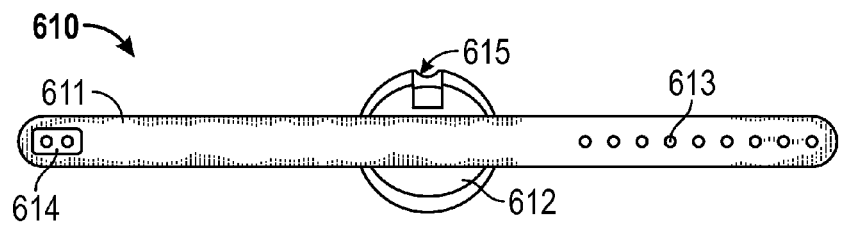
FIG. 31

ANTISEPTIC BRACELET

CROSS REFERENCE TO RELATED APPLICATIONS

This application claims the benefit of and incorporates by reference co-pending Patent Cooperation Treaty patent application number PCT/US2014/33703 filed on Apr. 10, 2014, which itself claimed the benefit of U.S. provisional patent application Ser. No. 61/810,308 filed Apr. 10, 2013.

BACKGROUND OF THE INVENTION

Field of the Invention

This invention relates to a wearable wrist accessory which provides for an efficient application of a germicidal substance to the hand of the wearer.

Description of the Prior Art

It is well known that the number one way infectious disease is spread is through hand contact. This is why the United States Center for Disease Control and governmental bodies all over the world recommend regular hand washing and the use of germicidal solutions. One problem with such a recommendation, however, is the fact that clean water and soap or germicidal solutions are not always immediately available to those who need to clean their hands at the time and place of need. Indeed, the creation of germicidal solutions in the first instance was in large part to address this problem as people are able to transport and or keep germicidal solutions in a convenient location for constant availability with much greater ease than water and soap.

While the proliferation of germicidal solutions helped address the problem, it did not completely solve it. A problem that still exists because the use germicidal solutions as presently implemented typically require a user to carry around a bottle containing such a solution or be in a close proximity to a germicidal solution or a wall mount or other stationary location. Furthermore, it is understood that one issue which arises with carrying and pulling out a bottle of germicidal solution can often lead to contamination of the surface of the bottle as it would typically require a full hand to pull out, open, dispense, and put away. In addition, in some social settings, it is frowned upon to pull out bottled germicidal solutions after meeting an individual or group and shaking hands.

Consequently, there remains an unmet need for germicidal transport and delivery device that can be inconspicuously carried and used to dispense a germicidal solution directly onto a user's palm. It would also be beneficial if such a germicidal transport and delivery device were structured to dispense antiseptic solution and otherwise operated with minimal touching requirements and specifically without requiring a full hand of the user. Such a germicidal transport and delivery device would be desirable to be worn by all types of people who come in contact for pathogens on a consistent basis and do not have constant access to water and soap, such as medical personnel, teachers, and kids. It would also be desirable for such a germicidal transport and delivery device be able to be discreetly worn by a user with long sleeves and to come in various shapes, sizes, colors, decorations and shapes to make it more appealing to wear when not being worn discreetly.

The Applicant's invention described herein provides for a wearable bracelet base having a removable pod containing an antiseptic solution that can be selectively dispensed directly onto a user's palm. The construction of the removable pod allows for it to be selectively integrated with the bracelet base that is worn on a user's wrist, with a dispensing tip on the removable pod oriented towards the base of the wearer's palm. Antiseptic solution is stored in a reservoir on the antiseptic bracelet such that by depressing the removable pod causes antiseptic solution to be forced through the dispensing tip.

SUMMARY OF THE INVENTION

A wearable antiseptic bracelet for use in allowing a wearer to selectively dispense an antiseptic solution directly on to their palm to enable disinfecting the user's hands. The antiseptic bracelet is to be worn on and around user's wrist near the base of the user's palm such that the antiseptic solution therein can be dispensed directly from the bracelet on to the user's palm. By storing the antiseptic solution in the antiseptic bracelet worn around the wrist, the user can discreetly carry the antiseptic solution at any desired time and in substantially any desired location, and is freed from having to carry a bottle of antiseptic solution or find a wall mount.

The antiseptic bracelet built in accordance with the preferred embodiment comprises a bracelet base and a removable pod. The bracelet base defines an elongated, flexible structure that is suitable to be looped around a user's wrist and includes a receiving slot. The removable pod defines a receptacle with a hollow interior for holding fluid material and a single outlet channel, and includes a discrete dispensing tip integral with the outlet channel through which material disposed in interior can selectively be dispensed. When the removable pod is in place in the receiving slot, it is oriented such that the dispensing tip extends beyond the perimeter of the bracelet base, thereby allowing fluid material exiting the dispensing tip to be directed to the palm of the arm on which the antiseptic bracelet is being worn.

It is an object of this invention to provide a germicidal storage and delivery device that is portable enough to be worn discreetly on the wrist of a user.

It is another object of this invention to provide to provide a germicidal storage and delivery device which can dispense a germicidal solution by merely depressing a certain spot on the device.

It is yet another object of this invention to provide a germicidal storage and delivery device which can dispense a germicidal solution directly onto a user's palm.

And yet another object of this invention is to a germicidal storage and delivery device having an outward appearance that can be manufactured in sizes, shapes, colors and styles without affecting the operation of the device.

These and other objects will be apparent to one of skill in the art.

BRIEF DESCRIPTION OF THE DRAWINGS

FIG. 9 is a front perspective view of an assembled antiseptic bracelet built in accordance with a second embodiment of the present invention.

FIG. 10 is an exploded front perspective view of an antiseptic bracelet built in accordance with a second embodiment of the present invention.

FIG. 11 is a cross section of a front perspective view of an assembled antiseptic bracelet built in accordance with a second embodiment of the present invention.

FIG. 12a is a side elevational view of the dispensing tip of an antiseptic bracelet built in accordance with a second embodiment of the present invention in a pre-actuated position with the pod body in shadow.

FIG. 12b is a side elevational view of the dispensing tip of an antiseptic bracelet built in accordance with a second embodiment of the present invention in an actuated position with the pod body in shadow.

FIG. 13a is a side elevational view of an assembled antiseptic bracelet built in accordance with a third embodiment of the present invention.

FIG. 13b is a top elevational view of an assembled antiseptic bracelet built in accordance with a third alternate embodiment of the present invention.

FIG. 14 is a front perspective view of an assembled antiseptic bracelet built in accordance with a fourth alternate embodiment of the present invention.

FIG. 15 is an exploded front perspective view of an antiseptic bracelet built in accordance with a fourth alternate embodiment of the present invention.

FIG. 16 is a cross section of a front perspective view of an assembled antiseptic bracelet built in accordance with a fourth alternate embodiment of the present invention.

FIG. 17 is a front perspective view of an assembled antiseptic bracelet built in accordance with a fifth embodiment of the present invention.

FIG. 18 is an exploded front perspective view of an antiseptic bracelet built in accordance with a fifth embodiment of the present invention.

FIG. 19 is a cross section of a front perspective view of an assembled antiseptic bracelet built in accordance with a fifth embodiment of the present invention.

FIG. 28 is a top plan view of a removable pod of an antiseptic bracelet built in accordance with the preferred embodiment of the present invention.

FIG. 29 is a side elevational view of a removable pod of an antiseptic bracelet built in accordance with the preferred embodiment of the present invention.

FIG. 30 is a top plan view of a bracelet base of an antiseptic bracelet built in accordance with the preferred embodiment of the present invention.

FIG. 31 is a bottom plan view of a bracelet base of an antiseptic bracelet built in accordance with the preferred embodiment of the present invention.

DETAILED DESCRIPTION OF THE INVENTION

Figure 1:
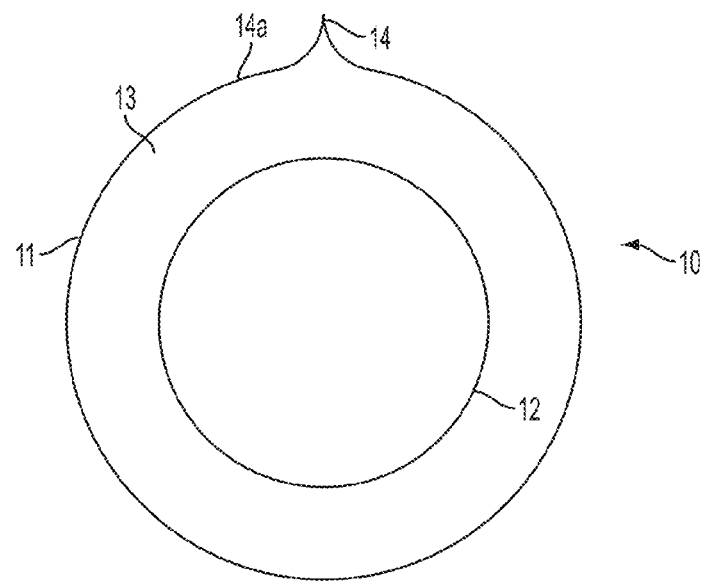
FIG. 1 is a side elevational view of an antiseptic bracelet built in accordance with a first embodiment of the present invention.
Figure 2:
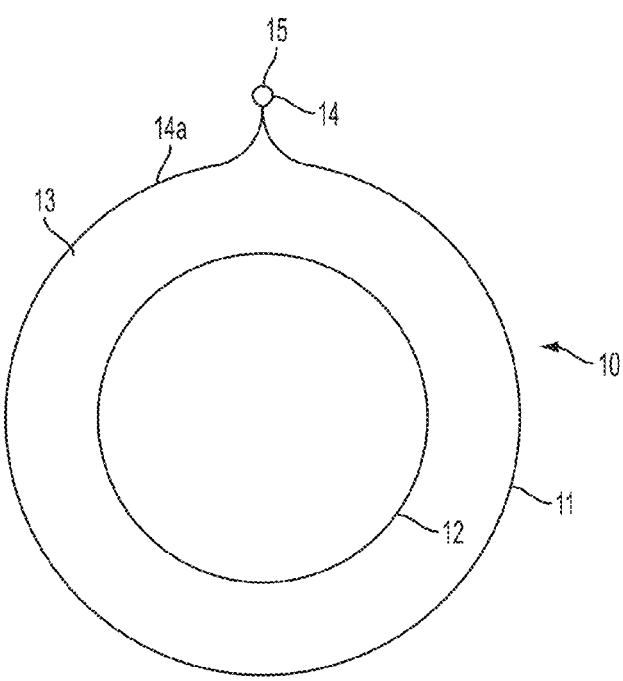
FIG. 2 is a side elevational view of an antiseptic bracelet built in accordance with a first embodiment of the present invention with antiseptic fluid being dispensed.

Referring now to the drawings, and in particular FIGS. 1 and 2, an antiseptic bracelet 10 built in accordance with an embodiment of the present invention is structured as a hollow ring body which accounts for the oval to circular shape of most human wrists and thus is configured so that the antiseptic bracelet 10 can be slid onto a user's wrist over the user's hand, rest comfortably on the user's wrist, and resist inadvertently sliding off the user's wrist over the user's hand. The ringed profile of the antiseptic bracelet 10 is defined by an elastic or semi-rigid, smooth outer surface 11 and an elastic, textured inner surface 12, and a bracelet body 13. It is contemplated that the anatomy of most humans is defined by an oval to circular shape wrist with a relatively smooth surface which is narrower that the widest point of the hand. The diameter of the inner surface 12, along with its texture and elasticity provide for the antiseptic bracelet 10's ability to be slid over the user's hand on the user's wrist rest comfortably on the user's wrist while resisting inadvertently sliding off the user's wrist over the user's hand.

The outer surface 11 includes a dispensing tip 14 and an air hole 14a, embodied in one embodiment as a pump valve which remains closed unless a user manually causing it to be opened. While the pump valve is closed, it prevents antiseptic solution stored in the antiseptic bracelet from seeping out of the dispensing tip 14. When the pump valve is opened, the antiseptic solution 14 stored in the antiseptic bracelet can be dispensed through the dispensing tip 14.

Figure 3:
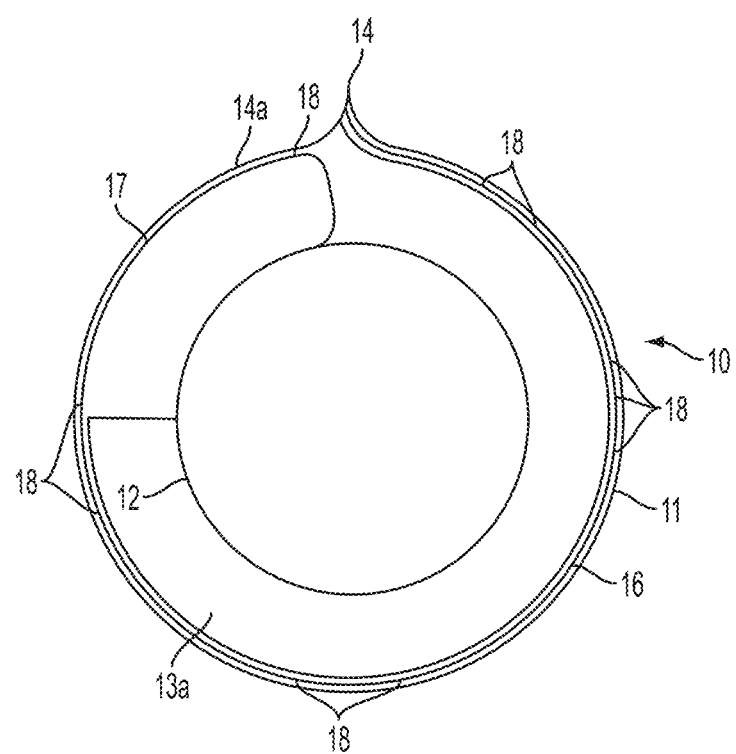
FIG. 3 is a cross section of a side elevational view of an antiseptic bracelet built in accordance with a first embodiment of the present invention.

Referring now to FIG. 3, the hollow interior 13a of the antiseptic bracelet is defined by the presence of an inner tube 16 and inner reservoir 17. The inner tube 16 and the inner reservoir 17 are comprised of a tubing structure which is attached to the interior wall of the outer surface 11 at several attachment points 18. The attachment points 18 assure that the inner tube 16 and the inner reservoir 17 cannot move freely and uncontrollably on the interior of the antiseptic bracelet 10. The inner reservoir 17 comprises a relatively large hollow structure with a deformable surface that is configured to hold a quantity of antiseptic fluid to be dispensed as desired by the user. It is contemplated that the inner reservoir 17 would be sized to be slightly smaller that the hollow interior 13a so as to allow it to hold a significant amount of antiseptic fluid when full and located in the hollow interior 13a just off to one side of the dispensing tip 14. As discussed below, this location allows for the creation of a pressure point that, when actuated by a user, mechanically causes both antiseptic fluid in the inner reservoir to be forced out and the pump valve of one embodiment to be opened so that antiseptic fluid is dispensed.

The inner tube 16 is a narrow rigid tube that runs along the interior wall of the outer surface 11 from the inner reservoir 17 to the dispensing tip 14. By way of this structure, it carries antiseptic fluid from the inner reservoir 17 to the dispensing tip 14. In typical operation, the inner tube 16 remains filled with antiseptic fluid substantially throughout its entire length, from its connection to the inner reservoir 17 to just below the dispensing tip 14 so that the operation of causing antiseptic fluid to be forced out of the inner reservoir 17 causes antiseptic fluid already in the inner tube 16 to be all pushed in a dispensing direction toward the dispensing tip 14, allowing for the antiseptic fluid closest to the dispensing tip 14 to be dispensed and all the antiseptic fluid in the inner tube 16 to be moved closer to the dispensing tip 14.

The antiseptic bracelet 10 is configured with a dispensing pressure point that substantially surrounds the air hole 14a. Pressure on the outer surface 11 in a direction intended to deform the elastic or semi-rigid outer surface 11 towards the inner surface 12 at or about this point causes the inner reservoir to be deformed inwardly, antiseptic fluid in the inner reservoir 17 to be forced into the inner tube 16, antiseptic fluid in the inner tube to all move towards the dispensing tip 14, and antiseptic fluid closest to the dispensing tip 14 to be dispensed. In the embodiment with the dispensing tip 14 comprising a pump valve, such pressure also causes the pump valve to slightly open so that antiseptic fluid can exit through the dispensing tip 14. When the pressure on the outer surface is removed, air can enter the hollow interior 13a through the air hole 14a and any deformation in the outer surface 11 returns. It is understood that in an alternate embodiment, any deformation in the hollow reservoir 17 remains such that with continued use, the hollow reservoir 17 becomes increasingly deformed until it empties and is substantially flat.

Figure 4:
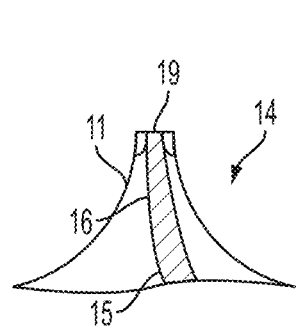
FIG. 4 is a cross section of a side elevational view of an embodiment of a dispensing tip of an antiseptic bracelet built in accordance with a first embodiment of the present invention.
Figure 5:
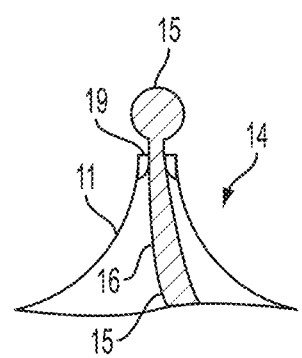
FIG. 5 is a cross section of a side elevational view of an embodiment of a dispensing tip of an antiseptic bracelet built in accordance with a first embodiment of the present invention with antiseptic fluid being dispensed.

Referring now to FIGS. 4 and 5, an embodiment of the dispensing tip 14 utilizes a rigid tab 19 which creates an inner lip around the exit point of the dispensing tip 14 to control dispensing of antiseptic fluid 15. In this embodiment, the inner tube 16 runs up to and terminates at the rigid tab 19. When there is no antiseptic fluid 15 exiting the inner tube 14, the structure of the rigid tab 19 results in the dispensing tip to be closed. When there is antiseptic fluid 15 being forced out of the inner tube 16, the antiseptic fluid 15 creates outward pressure on the rigid tab, which then causes the elastic or semi-rigid outer surface 11 to deform in the opposing direction, creating an opening through which antiseptic fluid 15 escapes the dispensing tip 14.

Figure 6:
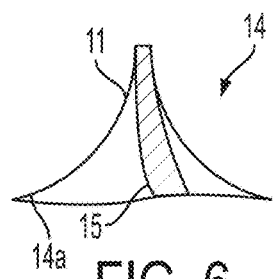
FIG. 6 is a cross section of a side elevational view of an embodiment of a dispensing tip of an antiseptic bracelet built in accordance with a first embodiment of the present invention.
Figure 7:
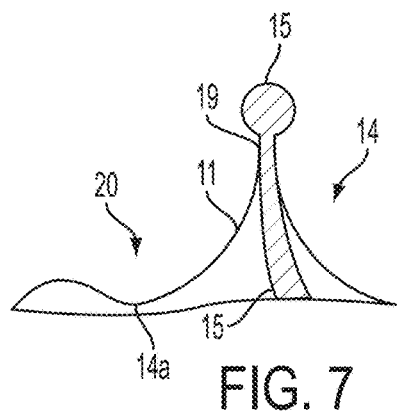
FIG. 7 is a cross section of a side elevational view of an embodiment of a dispensing tip of an antiseptic bracelet built in accordance with a first embodiment of the present invention with antiseptic fluid being dispensed.

Referring now to FIGS. 6 and 7, an embodiment of the dispensing tip 14 utilizes a pump valve which opens when pressure is put at or near the air hole 14a in an actuating direction 20. In this embodiment, pressure in the actuating direction 20 on the outer surface 11 cause both antiseptic fluid 15 to exit from the inner reservoir and the pump valve to open and antiseptic fluid to escape from the dispensing tip 14.

Figure 8:
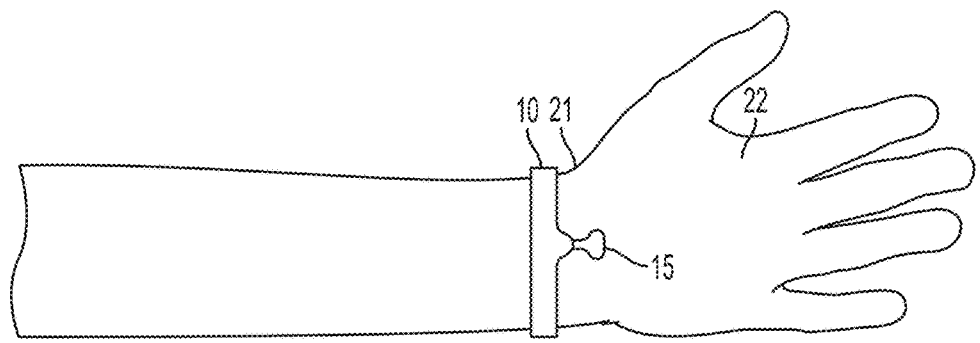
FIG. 8 is a top plan view of an antiseptic bracelet built in accordance with a first embodiment of the present invention being worn on a user's wrist.

Referring now to FIG. 8, the antiseptic bracelet 10 is worn by a user at or near the user's wrist 21. As a result, antiseptic fluid 15 exiting the antiseptic bracelet 10 is dispensed into the user's palm, where it can be spread and rubbed in so as to disinfect the user's hand.

In an alternate embodiment, the antiseptic bracelet includes a second inner tube disposed between the inner reservoir and the dispensing tip. In such an embodiment, the presence of the second inner tube allows solution to be dispensed by pressing anywhere along the bracelet due to its location inside the bracelet.

Referring now to FIGS. 9 through 12, an antiseptic bracelet 100 built in accordance with an embodiment of the present invention is shown having a bracelet band 110 connected to opposing sides of a dispensing pod 120. The bracelet band 110 is defined by an elongated band body 111 constructed of a flexible material. While the band body 111 is constructed in this embodiment of a flexible, molded plastic material, enabling it to be shaped to extend around and encircle a user's wrist when combined with the dispensing pod 120, it is contemplated that the band body 111 may be constructed of a flexible, elastic material which can be stretched over the wrist when combined with the dispensing pod 120. Further, it is understood that the band body 111 may be constructed of any material having properties which enable it to be worn and put on/taken off in such a manner as a conventional wristband, bracelet or watch.

The band body 111 includes two mirror image terminal end sections 112, each of which has a permanently attached locking member 113 disposed thereon. Each locking member 113 is a rigid, hooked structure having a flat end opposing a hook end. A respective locking member 113 is permanently attached to one of the terminal end sections 112 through its flat end being embedded in the particular terminal end section 112. In the disclosed embodiment, the locking members 113 are each molded into one of the terminal end sections 112 in a manner which enables the hook end to extend from the respective It is understood, however, that locking members 113 may be formed as part of the same molded body as the band body 111 or may be separate and permanently attached terminal end sections 112 through a conventional adhesive or fastener in addition to or in the alternative to the disclosed molding therein.

The dispensing pod 120 is defined by a hollow pod body 121 having a dispensing tip 122 disposed in a dispensing aperture 123 in the wall of the pod body 121 and two attachment flanges 124 extending from opposing sides of the pod body 121. The hollow nature of the pod body 121 forms an internal reservoir adapted to hold and retain fluid, such as an antiseptic solution. The exterior walls of the pod body 121 are constructed of a semi-rigid, deformable material, adapting the dispensing pod to allow a user to exert manual pressure on the wall and decrease the size of the internal reservoir, placing exiting pressure 126 on any fluid disposed inside the reservoir. The dispensing tip 122 acts as a value which enables only up to a set amount of fluid disposed in the pod body 121 to exit the pod body 121 when exiting pressure 126 is placed on the fluid In an alternate embodiment, the dispensing tip 122 is embodied as a press-in dispensing tip which can be moved to an actuated position 122b from a pre-actuated position 122a through the application of manual pressure in a compressing direction 125. In this regard, the dispensing tip 122 assists in regulating the flow of fluid through the dispensing aperture 123. When in the actuated position 122b, a hollow channel is formed in the dispensing tip 122, enabling fluid disposed in the pod body 121 to exit the pod body 121 when exiting pressure 126 is present on the fluid.

In this embodiment, it is understood that as fluid passes through the actuated dispensing tip 122, the fluid will exert pressuring in the direction opposing the compressing direction 125 and cause the dispensing tip to return to its pre-actuated position 122a. In the pre-actuated position 122a, fluid is blocked from passing through the dispensing tip 122, resulting in the pod body 121 functioning like a sealed chamber. In this regard, by placing the dispensing tip 122 to the actuated position 122b and the pod body 121 is deformed by a user through the application of manual pressure, fluid in the pod body 121 will be forced out of the dispensing tip 122 until the fluid passing through the dispensing tip 122 moves the dispensing tip back to the pre-actuated position 122a.

It is contemplated that the dispensing tip 122 is permanently attached in the dispensing aperture 123, but understood that the dispensing tip 122 may be removably disposed in the dispensing aperture 123 to enable the dispensing pod 120 to be refillable.

When the antiseptic bracelet is assembled, the dispensing pod 120 is releasably attached on both sides to the bracelet band 110 in a manner which creates a structural loop. The identical attachment flanges 124 on either side of the pod body 121 each include a receiving hole 124a therein. This receiving hole 124a is sized to receive the hook end of one of the locking members 113. In this regard, the bracelet band 110 can be attached to the dispensing pod 120 by orienting each locking member 113 vertically so that its hook end can hook onto and engage one respective receiving hole 124a. Once the hook end of each of the locking members 113 has engaged a respective receiving hole 124a, the locking member 113 can be oriented horizontally, as shown in FIG. 9, causing the locking member 113 to be secured to its respective attachment flange 124.

To partially or completely disconnect an assembled antiseptic bracelet 100, one or both the locking members 113 are moved to a vertical orientation and the hook end thereof is slid out of the respective receiving hole 124a in which the hook end was previously engaged. As it is contemplated that dispensing pods 120 may be disposable and replaceable, completely removing a dispensing pod 120 from a bracelet band 110 and replacing it with another dispensing pod 120 built in accordance with this embodiment of the present invention may be routinely desired. In addition, it is contemplated that simply putting on or taking off the antiseptic bracelet 100 will include assembling or disassembling at least one side of the bracelet band 110 to or from the dispensing pod 120, respectively.

In the disclosed embodiment, the dispensing pod 120 is sized to hold 0.25 ounces of an antiseptic solution.

It one embodiment of the antiseptic bracelet or the dispensing pod of an antiseptic bracelet is disposable when all antiseptic fluid is removed therefrom. A refillable embodiment, however, may also desirable to some users and is implemented with the addition of an antiseptic fluid applicator with a tip that can fit into the dispensing tip of the antiseptic bracelet and create sufficient force to cause additional antiseptic fluid to enter into the reservoir.

It is contemplated that a variety of sizes is necessary for different sized users as with nearly any wrist accessory. As such, it is understood that the exterior of the antiseptic bracelet, particularly the outer surface, can be manufactured in varying sizes, shapes, colors and styles without affecting the operation of the device. Further, in embodiments having detachable dispensing pods, it is contemplated that the dispensing pods and bracelet bands can be manufactured in different colors so as to enable a user to mix and match colors as desired.

Referring now to FIGS. 13a and 13b, an antiseptic bracelet 50 built in accordance an embodiment of the present invention is shown as a hollow silicone gel bracelet body 51 having a dispensing hole 52 disposed on a side wall thereon. In this embodiment, the interior of the bracelet body 51 defines a dispensing pod which is embodied as a hollow channel which spans through the bracelet body 51 and leads to the dispensing hole 52 in a similar manner as the inner tube in FIG. 3. The hollow channel enables the bracelet body 51 to hold fluid, such as an antiseptic solution, therein and the dispensing hole 52 enables fluid held in the bracelet body 51 to be dispensed by a user. Fluid is dispensed by a user by employing manual pressure on the bracelet body 51 to cause it to deform, forcing fluid in the bracelet body 51 out of the dispensing hole 52

Referring now to FIGS. 14 through 16, an antiseptic bracelet 200 built in accordance with an embodiment of the present invention is shown having a bracelet band 210 permanently connected to opposing sides of a dispensing pod 220. The primary components of the antiseptic bracelet 200 in this embodiment, except that the opposing attachment flanges 224 on the sides of the hollow pod body 221 of the dispensing pod 220 are each molded into one of the terminal end sections 212 of the bracelet band 210. In this regard, the bracelet band 210 and the dispensing pod 220 are permanently attached to one another to form a loop and the bracelet band 210 is constructed of a flexible material which can enable it to be stretched over a user's wrist due to be put on or taken off.

Referring now to FIGS. 17 through 19, an antiseptic bracelet 300 built in accordance with an embodiment of the present invention is shown having a bracelet band 310 connected a dispensing pod 320. In this embodiment, the bracelet band 310 is defined as a half bracelet curve body 311 constructed of an elastic material which enables it to be snapped onto a user's wrist. The curve body 311 includes a T-slot 312 on its surface which enables it to receive and hold the dispensing pod 320. The dispensing pod 320 is defined by a deformable hollow pod body 321 having a press-in dispensing tip 322 disposed in a dispensing aperture 323 in the wall of the pod body 321 and T-plug 324 extending from the bottom of the pod body 321. The T-plug 324 is sized to engaged the T-slot 312, enabling the dispensing pod 320 to be removably attached to the bracelet band 310. The dispensing pod 320 in this embodiment is sized to hold 0.2 ounces of fluid.

Figure 22:
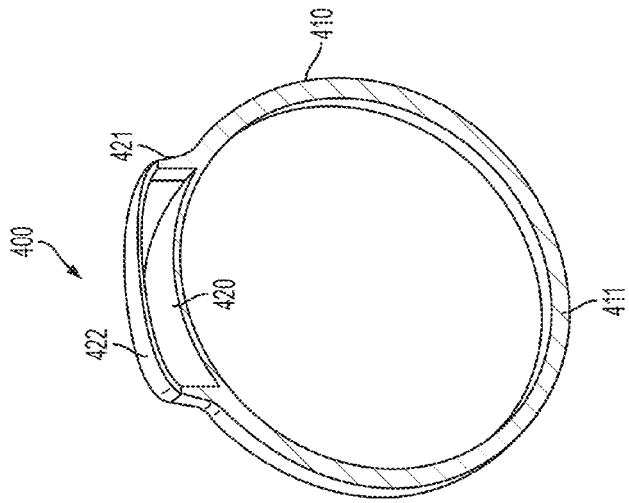
FIG. 22 is a cross section of a front perspective view of an assembled antiseptic bracelet built in accordance with a sixth embodiment of the present invention.
Figure 21:
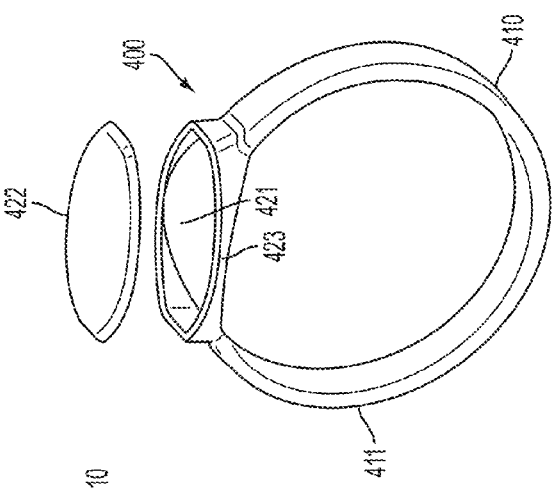
FIG. 21 is an exploded front perspective view of an antiseptic bracelet built in accordance with a sixth embodiment of the present invention.
Figure 20:
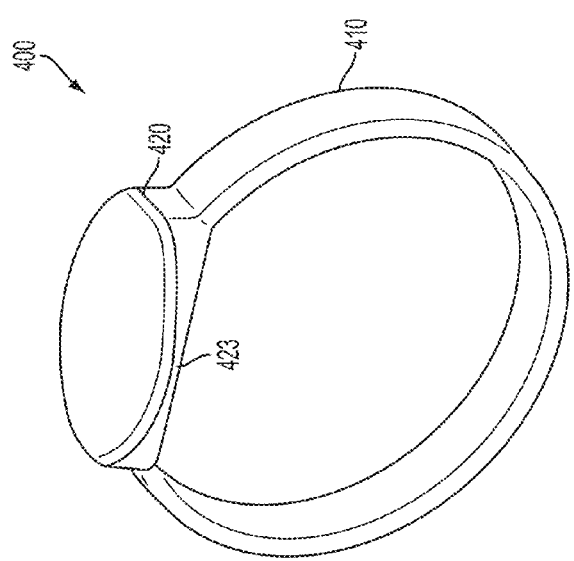
FIG. 20 is a front perspective view of an assembled antiseptic bracelet built in accordance with a sixth embodiment of the present invention.

Referring now to FIGS. 20 through 22, an antiseptic bracelet 400 built in accordance with an embodiment of the present invention is shown having a bracelet band 410 connected a dispensing pod 420. In this embodiment, the dispensing pod 420 includes a pod bowl 421 and a flexible, thin walled cap 422 sized to fit on top of the pod bowl 421 to form a hollow enclosure. The bracelet band 410 is defined by an elongated band body 411 constructed of a flexible, elastic material and having the pod bowl 421 integrated thereon. The pod bowl 421 is additionally includes a dispensing aperture 423 in its side wall, fluid contained in the dispensing pod 420 to be selectively dispensed. Fluid is dispensed through the application of manual pressure on the walled cap 422, deforming it to force fluid out of the dispensing aperture 423. In this embodiment, the dispensing pod 420 is sized to hold 0.2 ounces of fluid.

Figure 25:
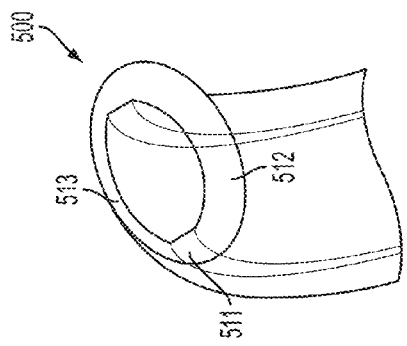
FIG. 25 is a cross section of the dispensing tube of an antiseptic bracelet built in accordance with a seventh embodiment of the present invention.
Figure 24:
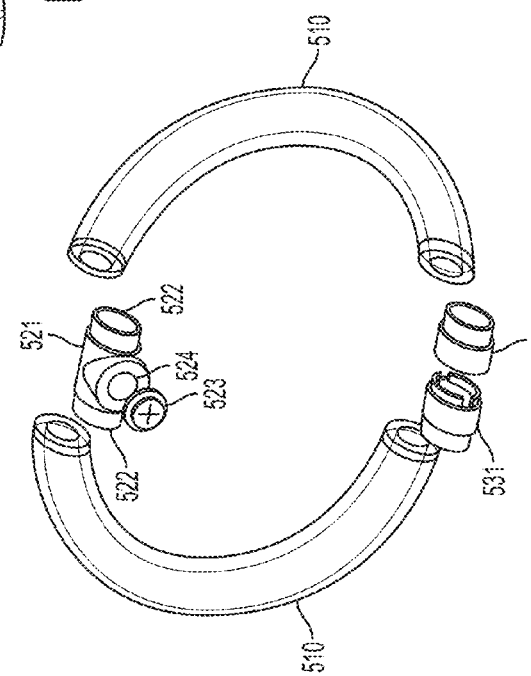
FIG. 24 is an exploded front perspective view of an antiseptic bracelet built in accordance with a seventh embodiment of the present invention.
Figure 23:
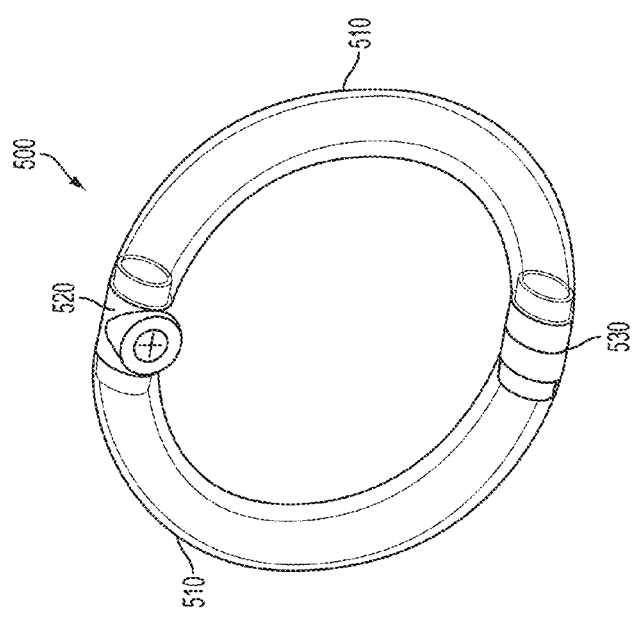
FIG. 23 is a front perspective view of an assembled antiseptic bracelet built in accordance with a seventh embodiment of the present invention.
Figure 26:
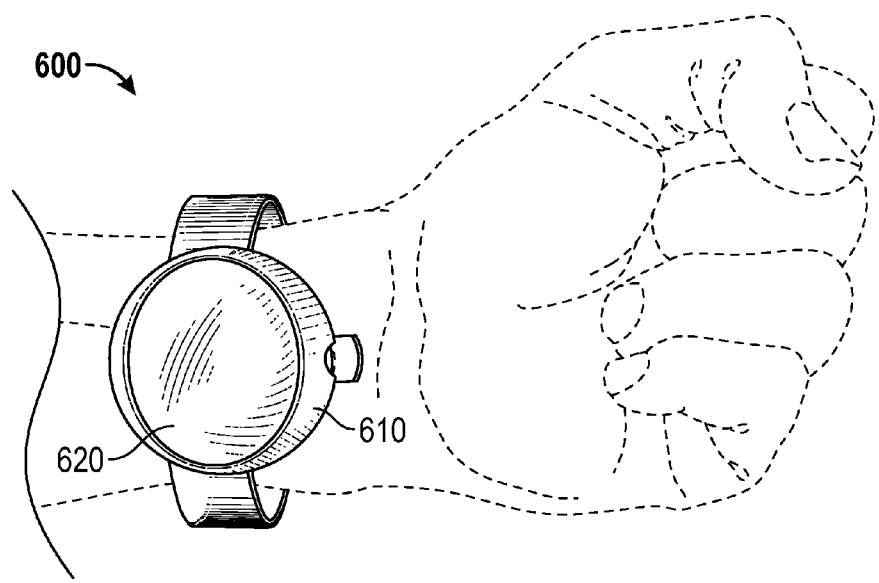
FIG. 26 is a top plan view of an antiseptic bracelet built in accordance with the preferred embodiment of the present invention shown in place on a wearer.
Figure 27:
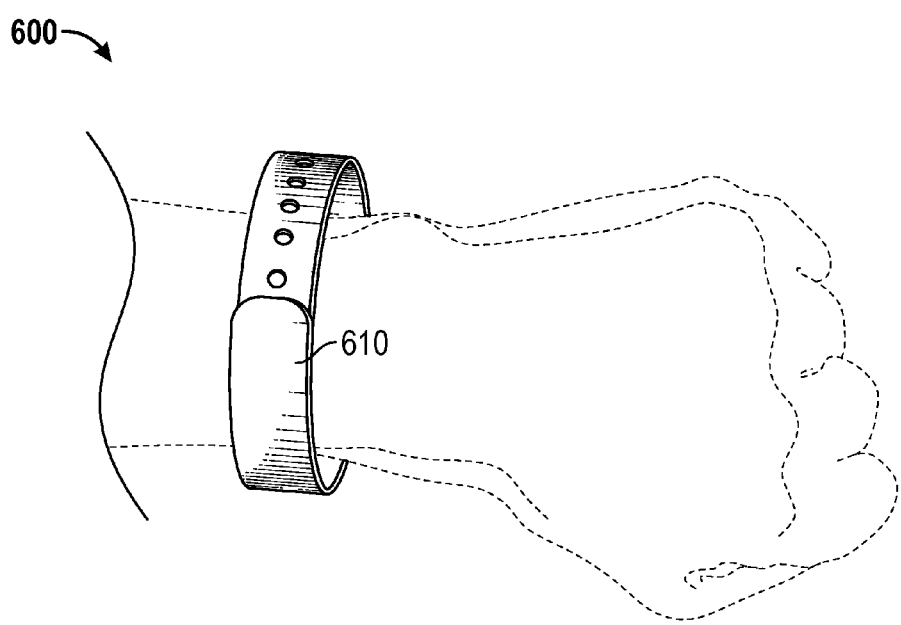
FIG. 27 is a bottom plan view of an antiseptic bracelet built in accordance with the preferred embodiment of the present invention shown in place on a wearer.

Referring now to FIGS. 23 through 25, an antiseptic bracelet 500 built in accordance with an embodiment of the present invention is shown having two identical bracelet band sections 510, each connected at one end to a dispensing connector 520 and at the other end to a bottom connector 530. Each band section 510 is defined by an section of extruded flexible tubing having a relatively thick side 511 and bottom (the side that contacts a wearer's wrist) walls 512 to allow the tube to bend without kinking and a relatively thin top (the wall opposite the side the contacts a wearer's wrist) wall 513 to enable it to be selectively deformed by a user through the application of manual pressure thereon. The extruded nature of the band sections 510 enable fluid to be held stored therein for subsequent dispensing.

The dispensing connector 520 is defined by a rigid joint connector 521 having connector outlets 522 on opposing sides and including dispensing tip 523 disposed in a dispensing aperture 524. When the antiseptic bracelet 500 is assembled, one end of each of the band sections 510 is slid onto and attached to one of the connector outlets 522 of the dispensing connector 520. The dispensing tip 523 is defined by a conventional silicone valve spout which enables fluid under pressure to pass through. In this regard, the dispensing tip 523 assists in regulating the flow of fluid through the dispensing aperture 524. When manual pressure is exerted on a location of the top wall 513, deforming it and forcing fluid therefrom, fluid can be forced out of the dispensing tip 523.

The bottom connector 530 is defined by a male connector section 531 and a female connector section 532 which are structured to be releasably attached to one another. When the antiseptic bracelet 500 is assembled, the male connector section 531 is slid onto and attached to one of the band sections 510, the female connector section 532 is slid onto and attached to the other band section 510, and the male connector section 531 and a female connector section 532 are attached to one another. When the band sections 510 are attached to both the dispensing connector 520 and the bottom connector 530, the antiseptic bracelet 500 is formed as a loop structure having a hollow channel for holding fluid therein. The hollow channel of the antiseptic bracelet 500 is sized to hold 0.4 ounces of fluid.

Referring now to FIGS. 26 through 31, an antiseptic bracelet 600 built in accordance with the preferred embodiment of the present invention is shown having a bracelet band 610 and a removable dispensing pod 620. The bracelet band 610 defines an elongated, flexible band body 611 that has a receiving slot 612 centrally disposed thereon. The band body 611 which includes a first end and a second end, is sized to be looped and fastened around a user's wrist and includes a plurality of fastening apertures 613 therein, sequentially aligned from the first end as well as dual fastening nubs 614 disposed at the second end. It is contemplated that the dual fastening nubs 614 are sized to be removably inserted into adjacent fastening apertures 613 in order to releasably secure the band body 611 in place on a wearer's wrist at a position adjacent to the base of the wearer's palm.

The removable dispensing pod 620 defines a discrete receptacle 621 with a deformable exterior and a hollow interior and a single outlet channel 622. The receptacle 621 is thereby suitable to hold a fluid material therein and allow fluid material held therein to be directed through the outlet channel 622 when sufficient mechanical pressure is placed on the exterior of the receptacle 621 to cause the exterior to deform a certain amount, and the volume of the interior to decrease to a quantity that corresponds to the deformation. A dispensing tip 623 which defines a one way valve is integral with the outlet channel 622, positioned such that any fluid material directed through the outlet channel 622 must pass through the dispensing tip 623 and out of the removable pod 620. In some embodiments, the dispensing tip 623 is molded into the outlet channel 622, while in other embodiments the dispensing tip 623 defines a discrete member which has been fixably fastened in the outlet channel 622 (by, for example a threaded exterior surface which corresponds to a threaded interior surface in the outlet channel 622).

It is appreciated that when sufficient pressure is exerted on the receptacle 621 to reduce its volume, the inability for air to replace the volume of fluid dispensed results in the amount of deformation of the exterior to be permanent. Accordingly, it is contemplated that in operation the receptacle 621 may be repeatedly deformed to repeatedly dispense fluid, with its internal volume becoming lower and lower until the interior volume is reduce to substantially zero (which would also mean there was substantially no fluid remaining therein).

It is contemplated that once the receptacle 621 of a given dispensing pod 620 is empty, a user can simply remove the used dispensing pod 620 and replace it with a different dispensing pod 620 that is new or otherwise not empty.

The dispensing pod 620 and receiving slot 612 are correspondingly sized such that the dispensing pod 620 may be removably placed in and held by the receiving slot 612. The receiving slot 612 includes a tip slit 615 structured to receive the dispensing tip 623 and orient the dispensing tip 623 such that the dispensing tip 623 extends beyond the perimeter of the bracelet band 610 and receiving slot 612 and is directed perpendicular to the length of the bracelet band 610, thereby allowing fluid material exiting the dispensing tip 623 to be directed towards the base of a wear's palm on the arm on which the antiseptic bracelet 600 is being worn. Advantageously, this design allows a wearer to use their off-hand (the hand of the arm not wearing the bracelet 600) to dispense fluid directly on to their on-hand (the hand of the arm wearing the bracelet 600) and, if desired simply rub their hands together to disinfect both hands.

The instant invention has been shown and described herein in what is considered to be the most practical and preferred embodiments. It is recognized, however, that variations and departures may be made therefrom within the scope of the inventions and that obvious modifications will occur to a person of ordinary skill in the art.

What I claim is:

1. An antiseptic bracelet apparatus for storing and selectively dispensing fluid, comprising:
   an elongated wristwear structure configured to be selectively fastened to one arm of a wearer in a location that is adjacent to the base of a palm of the hand on the arm to which the wristwear structure is fastened;
   wherein said wristwear structure includes a receiving slot disposed thereon;
   a dispensing pod defining a discrete receptacle having at least one outlet channel, wherein said dispensing pod is removably attached to said wristwear structure through the receiving slot and configured to hold fluid therein as well as selectively direct fluid held therein through said at least one outlet channel;
   a dispensing tip integral with said dispensing pod such that any fluid which is held in said dispensing pod and directed through said at least one outlet channel exits the dispensing pod through the dispensing tip, wherein said dispensing tip is oriented orthogonally relative to the length of said wristwear structure such that fluid exiting the dispensing pod therefrom is directed beyond the edge of the wristwear structure; and wherein the receiving slot includes a tip slit adapted to receive the dispensing tip when the dispensing pod is attached to the receiving slot in the orthogonal orientation relative to the length of said wristwear.

2. The antiseptic bracelet apparatus of claim 1, wherein:
said wristwear structure defines a bracelet band having a flexible, elongated band body with a first end and an opposing second end; and
said receiving slot is centrally disposed on said bracelet band.

3. The antiseptic bracelet apparatus of claim 2, wherein said band body includes a plurality of fastening apertures sequentially aligned from the first end and dual fastening nubs disposed at the second end, thereby enabling the bracelet band to be releasably fastened to one arm of a wearer.

4. The antiseptic bracelet apparatus of claim 1, wherein said receptacle defining the dispensing pod includes a deformable exterior and a hollow interior, thereby enabling the dispensing pod to hold a fluid material therein and allow fluid material held therein to be directed through the outlet channel when mechanical pressure is placed on the exterior of the receptacle that causes the exterior to deform a first amount and the volume of the interior to decrease to a first quantity that corresponds to the first amount of deformation.

5. The antiseptic bracelet apparatus of claim 1, wherein said dispensing tip defines a discrete one way valve positioned in the at least one outlet channel.

6. An antiseptic bracelet apparatus for storing and selectively dispensing fluid, comprising:
a bracelet band having a flexible, elongated band body with first end and an opposing second end as well as a receiving slot centrally disposed thereon, wherein said bracelet band is configured to be selectively fastened to one arm of a wearer in a location that is adjacent to the base of a palm of the hand on which the bracelet band is fastened;

a dispensing pod defining a discrete receptacle having at least one outlet channel, wherein said dispensing pod is removably integrated with said bracelet band through the receiving slot and configured to hold fluid therein as well as selectively direct fluid held therein through said at least one outlet channel; and a dispensing tip integral with said dispensing pod such that any fluid which is held in said dispensing pod and directed through said at least one outlet channel exits the dispensing pod through the dispensing tip, wherein said dispensing tip is oriented orthogonally relative to the length of said bracelet band such that fluid exiting the dispensing pod therefrom is directed beyond the edge of the bracelet band; and wherein the receiving slot includes a tip slit adapted to receive the dispensing tip when the dispensing pod is attached to the receiving slot in the orthogonal orientation relative to the length of said wristwear.

7. The antiseptic bracelet apparatus of claim 6, wherein said band body includes a plurality of fastening apertures sequentially aligned from the first end and dual fastening nubs disposed at the second end, thereby enabling the bracelet band to be releasably secured to one arm of a wearer.

8. The antiseptic bracelet apparatus of claim 6, wherein said receptacle defining the dispensing pod includes a deformable exterior and a hollow interior, thereby enabling the dispensing pod to hold a fluid material therein and allow fluid material held therein to be directed through the outlet channel when mechanical pressure is placed on the exterior of the receptacle that causes the exterior to deform a first amount and the volume of the interior to decrease to a first quantity that corresponds to the first amount of deformation.

9. The antiseptic bracelet apparatus of claim 6, wherein said dispensing tip defines a discrete one way valve positioned in the at least one outlet channel.

* * * * *